United States Patent
Ujvári et al.

(10) Patent No.: US 12,020,439 B2
(45) Date of Patent: Jun. 25, 2024

(54) COMPUTER-IMPLEMENTED METHOD FOR VISUALIZING A LAG TIME IN A TRANSFERRED IMAGE AND DEVICE FOR OUTPUTTING AN IMAGE

(71) Applicant: Siemens Healthcare GmbH, Erlangen (DE)

(72) Inventors: Tamás Ujvári, Forchheim (DE); Gaurav Tripathi, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/230,875

(22) Filed: Aug. 7, 2023

(65) Prior Publication Data
US 2024/0070869 A1     Feb. 29, 2024

(30) Foreign Application Priority Data
Aug. 30, 2022   (DE) ................... 10 2022 208 956.1

(51) Int. Cl.
*G06T 7/11* (2017.01)

(52) U.S. Cl.
CPC ...... *G06T 7/11* (2017.01); *G06T 2207/30204* (2013.01)

(58) Field of Classification Search
CPC .................. G06T 7/11; G06T 2207/30204
See application file for complete search history.

(56) References Cited

U.S. PATENT DOCUMENTS

| | | | | |
|---|---|---|---|---|
| 7,201,321 B2 * | 4/2007 | He | ..................... | G06K 7/10861 |
| | | | | 235/462.05 |
| 8,688,579 B1 * | 4/2014 | Ethington | ............ | G06V 30/416 |
| | | | | 705/42 |
| 10,300,888 B1 * | 5/2019 | Gilbert-Eyres | ........ | H04N 7/185 |

(Continued)

FOREIGN PATENT DOCUMENTS

| | | |
|---|---|---|
| CN | 107566827 A | 1/2018 |
| CN | 111047519 A | 4/2020 |

(Continued)

OTHER PUBLICATIONS

Beck, Thomas; IEC, ISO. "62304: Medical Device Software-Software Life-Cycle Processes. Edition 1.1 Jun. 2015." IEC: Geneva, Switzerland. Mar. 22, 2022.. pp. 1-176.

*Primary Examiner* — Mia M Thomas
(74) *Attorney, Agent, or Firm* — Lempia Summerfield Katz LLC (57) ABSTRACT

A method is provided for visualizing a lag time in an image. The method includes: specifying a first marker by the transmit facility that is dependent on the first processing instant; processing original image data of the image by the transmit facility, wherein a part of the original image data that describes a specified image segment is modified by the first marker to provide modified image data of the image; transferring the modified image data from the transmit facility to the receive facility; specifying a second marker by the receive facility that is dependent on the second processing instant; processing the modified image data by the receive facility, wherein at least part of the modified image data is modified by an overlay of the second marker with the modified image data in the image segment to provide final image data of the image; and outputting the final image data.

12 Claims, 2 Drawing Sheets

(56) References Cited

U.S. PATENT DOCUMENTS

| | | | |
|---|---|---|---|
| 2010/0222144 A1* | 9/2010 | Ohba | A63F 13/54 |
| | | | 463/35 |
| 2011/0035326 A1* | 2/2011 | Sholl | G06Q 30/018 |
| | | | 705/317 |
| 2013/0113954 A1 | 5/2013 | Nagel et al. | |
| 2014/0128735 A1* | 5/2014 | Newell | A61B 8/56 |
| | | | 600/443 |
| 2015/0039462 A1* | 2/2015 | Shastry | G06Q 30/0631 |
| | | | 705/26.81 |
| 2015/0121439 A1* | 4/2015 | Wellen | H04N 21/8456 |
| | | | 725/109 |
| 2019/0197818 A1* | 6/2019 | Rosander | G07F 17/3209 |
| 2020/0117957 A1 | 4/2020 | Birkhold et al. | |
| 2021/0217245 A1* | 7/2021 | Akman | A63H 30/04 |
| 2021/0266617 A1* | 8/2021 | Ropke | G06T 1/0085 |
| 2022/0293262 A1* | 9/2022 | Beck | A61B 5/0205 |
| 2022/0294975 A1* | 9/2022 | Popovic | H04N 23/90 |
| 2023/0079964 A1* | 3/2023 | Schmuland | B22F 12/45 |
| | | | 419/1 |
| 2023/0118280 A1* | 4/2023 | Heidmann | G06V 20/64 |
| | | | 345/419 |

FOREIGN PATENT DOCUMENTS

| | | | | |
|---|---|---|---|---|
| DE | 102011117659 A1 | 5/2013 | | |
| DE | 102016013502 A1 | 5/2017 | | |
| DE | 102016202620 A1 | 8/2017 | | |
| EP | 2040145 A1 * | 3/2009 | | A63F 13/00 |
| JP | 2013247489 A | 12/2013 | | |

* cited by examiner

FIG 2

| | | | |
|---|---|---|---|
| 1 - transmit facility | 15 - network | 23 - leading edge | 31 - operating device |
| 2 - receive facility | 16 - time server | 24 - trailing edge | 32 - actuator |
| 3 - plurality of images | 17 - marker motif | 25 - remaining portion | 41 - information |
| 8 - image segment | 18 - axis of rotation | 26 - gradient | 42 - image |
| 12 - display facility | 19 - rotation | 27 - leading edge | 43 - overlay representation |
| 13 - communication facility | 20 - second marker motif | 28 - trailing edge | 44 - overlay representation |
| 14 - communication facility | 21 - axis of rotation | 29 - remaining portion | 45 - overlay representation |
| | 22 - gradient | 30 - imaging facility | 46 - segment |
| | | | 47 - segment |
| | | | 48 - segment |
| | | | 49 - segment |
| | | | 50 - segment |
| | | | 51 - segment |
| | | | 52 - rotation |

FIG 3

COMPUTER-IMPLEMENTED METHOD FOR VISUALIZING A LAG TIME IN A TRANSFERRED IMAGE AND DEVICE FOR OUTPUTTING AN IMAGE

The present patent document claims the benefit of German Patent Application No. 10 2022 208 956.1, filed Aug. 30, 2022, which is hereby incorporated by reference in its entirety.

TECHNICAL FIELD

The disclosure relates to a computer-implemented method for visualizing a lag time in at least one image transferred from a transmit facility to a receive facility, wherein the lag time describes a time interval between processing of the image by the transmit facility at a first processing instant and processing of the image by the receive facility at a second processing instant. The disclosure additionally relates to a device for outputting at least one image.

BACKGROUND

On transferring image data between a transmit and receive facility, a lag time occurs which may vary greatly, in particular on transfer via public networks, for example, over the internet or virtual private networks or the like based thereon. In the case of purely passive image viewing, such lags may be compensated by using a sufficiently large buffer memory. However, in applications in which image transfer is intended to be part of a control system, for example, for remotely controlling robots or tools, as are in principle known from the fields of workpiece machining or telemedicine, severe lags or major fluctuations in image transfer may result in operating errors or impairment of hand-eye coordination in particular if a user who is being guided by the received image data does not identify or incorrectly estimates such a lag or fluctuation or the extent of the lag or fluctuation.

Applications in which processes are to be remotely controlled on the basis of video data are therefore, at least where incorrect operation may result in considerable costs or even a risk to health, only implementable if either sufficiently short and stable transfer times may be guaranteed, for example, by using dedicated closed networks, which are however unavailable in many use cases or result in elevated costs, or if the lag time between processing by the transmit facility and by the receive facility, or at least a limit value arising from this lag time being exceeded, may be sufficiently robustly identified.

However, since erroneously failing to identify a severe or fluctuating lag time may, in some telemedicine use cases, result in a considerable risk to a patient's health, a sufficiently high level of first-failure safety would be necessary for all components involved in the case of exclusively automated monitoring of the lag time. This may be achieved by using sufficiently first-failure safe components, such that software components involved would, for example, have to meet software safety class C to international standard IEC 62304 and it may be necessary to avoid using commercial hardware and software, or by taking additional steps, for example, redundancy. For example, watchdog mechanisms which exhibit sufficient first-failure safety or are validated by additional mechanisms may be used to monitor internal time counters.

It is in principle also possible for experienced users to be able to identify simply from viewing an image data stream when extended lags occur between individual images. In medical imaging or indeed other areas of application, only slight movements in the image over extended periods of time are frequently identifiable, such that for example a short additional lag until display of a further image is not in every case straightforwardly identified even by experienced users.

SUMMARY AND DESCRIPTION

The scope of the present disclosure is defined solely by the appended claims and is not affected to any degree by the statements within this summary. The present embodiments may obviate one or more of the drawbacks or limitations in the related art.

The object of the disclosure is thus to assist a user in estimating a lag time or in identifying long lag times between image processing by the transmit facility and by the receive facility, whereby the intention is in particular to enable the user to be able to robustly identify fluctuations in transfer time, as a result of which, even if such fluctuations cannot be automatically identified, incorrect operation by the user due to this lag may be avoided.

The object is achieved by a method of the above-mentioned type. The method includes specifying a first marker by the transmit facility, wherein the first marker is dependent on the first processing instant. The method further includes processing original image data of the image by the transmit facility such that that part of the original image data which describes a specified image segment is modified (e.g., added or replaced) by the first marker or an overlay of the first marker with the original image data in this image segment, in order to provide modified image data of the image. The method further includes transferring the modified image data from the transmit facility to the receive facility. The method further includes specifying a second marker by the receive facility, wherein the second marker is dependent on the second processing instant. The method further includes processing the modified image data by the receive facility such that at least part of the modified image data in the specified image segment is modified (e.g., added or replaced) by an overlay of the second marker with the modified image data in the image segment in order to provide final image data of the image. The method further includes outputting the final image data by a display facility in order to visualize the lag time in the image segment of the image.

In the method, the first and second markers are overlaid in the image segment. Since the first and second markers are dependent on the respective processing instant, it is possible on the basis of this overlay for the lag time between these instants, and thus in particular the transfer time between the transmit and receive facility that may dominate at least the variable proportion of this lag time, to be visualized for the user viewing the image on the display facility.

Suitable selection of the first and second markers allow, as is explained in greater detail below, in particular intuitive marking, such that lag times above a tolerance time may be marked by superimposing red bars or circle segments and sufficiently small lag times by superimposing green bars or circle segments, wherein the length of the bar or the angle spanned by the circle segment may indicate the extent to which the tolerance time is exceeded or undershot. A user may thus identify at first glance when elevated lag times are currently present and thus, for example, remote control based on the current image may be avoided.

At the same time, suitable selection of the markers or their dependency on the respective processing instant may provide that, on display of an image sequence or of an image data stream of the display facility, the image display remains in motion in the segment, whereby freezing of the image may also be immediately identified by the user and thus any incorrect operation arising therefrom may also be avoided.

The transmit facility and the receive facility may, in each case, have an internal timer, wherein in the case of modern timers it may be assumed that, due to tolerances, only very small time deviations will occur even over extended periods of time. Time synchronization may proceed using per se known synchronization protocols, for example, NTP, SNTP, PTP, or the like. A pair of transmit and receive facilities may be directly synchronized with one another, wherein one of these facilities may serve as the master for this synchronization. Both the transmit and the receive facility, however, may be synchronized with at least one external time server. This may be advantageous if a transmit facility is intended to cooperate with various receive facilities and/or vice versa. Errors that may be anticipated with internal timers are at most slow drifting or sudden jumps. Both are inherently identifiable as errors in the explained method and errors in time synchronization may be identified in advance of image transfer. Internal timer errors would indeed be problematic if they were to approximately compensate actually occurring fluctuations or increases in lag time, but this is extremely unlikely.

The described procedure for visualizing the lag time additionally has the advantage that, apart from an initial time synchronization, visualization itself solely requires unidirectional communication, namely from the transmit facility to the receive facility, and that no further information need be transferred in addition to the modified image data of the image in order to enable such visualization. Since parts of the image or of the image data stream are used for visualizing the lag time, if the image or image data stream is recorded it is also subsequently possible to understand what lags occurred, such that it is, for example, also possible to document that or whether a user responded reasonably to the lag which occurred. Since the method is based directly on the images or the video data stream themselves/itself and no additional components or mechanisms are required, the method is inherently safe.

Overlaying of the first marker with the original image data and/or of the second marker with the modified image data may be an additive or subtractive overlay. In the case of an additive overlay, the color values of the respective marker and the color values of the respective image data may be summed, for example. It may be particularly advantageous for the second marker to contain color information solely in color channels that are not used in the first marker. For example, the first marker may have non-zero entries solely in the green color channel and the second marker non-zero entries solely in the red color channel. If this is the case, on overlaying, the previous value in the original image or in the original or modified image data in the color channel used by the respective marker may also simply be overwritten by the value specified by the marker or the like.

The first marker may be specified such that the first marker varies periodically with the first processing instant. Additionally, or alternatively, the second marker may be specified such that the second marker varies periodically with the second processing instant. The periodicity with which the first and second markers vary may here be identical. In other words, the first or second markers used may in each case repeat at a fixed time interval, for example, at a time interval of a few hundred ms or 1 s or in a range of 100 ms-1 s. If a periodicity of 1 s is used, for example, this may indeed mean that it is no longer possible, solely on the basis of the image, to differentiate between a lag time of 200 ms and a lag time of 1200 ms. However, since very long lag times may be straightforwardly identified at least in an image sequence, this may nevertheless be advantageous in terms of intuitive comprehensibility of the marker. A substantially unchanged overlay representation due to the periodicity would only arise in an image sequence in the event of an abrupt change in lag time, wherein the size of the change approximately matches the period duration and wherein the lag time before and after this abrupt change remains substantially constant in each case. This is very improbable and such instability in image transfer may be identified, for example, by a suitable marker, as is explained in greater detail below.

It is also possible for a plurality of first and second markers to be used that vary with mutually differing periods. If in each case a first and a second marker with an identical period duration are overlaid, it is thus possible, on the basis of overlaying the markers with a shorter period duration, to represent the lag time with great accuracy and, on the basis of overlaying the markers with a longer period duration, to eliminate ambiguities due to the shorter periodicity at least when the lag time is less than the longer period. The various first and second markers may be represented as concentric rings. Functionally, this corresponds to using an hour and a minute hand of a clock. Different periodicities which may be used are for example 1 s and 5 s.

The first marker may be specified such that, in dependency on the first processing instant, a specified first marker motif is on the one hand rotated with respect to the image segment and/or on the other hand is displaced at least in portions. Additionally, or alternatively, the second marker may be specified such that, in dependency on the second processing instant, a specified second marker motif is on the one hand rotated with respect to the image segment and/or on the other hand is displaced at least in portions.

In the case of rotation of the respective marker motif, it may be possible to use marker motifs that are circular, circular segment-shaped, circular ring-shaped, or circular ring segment-shaped, which may be rotated about an axis of rotation around the center point of the circle. Thus, a rotating circle with a color gradient or a saturation or lightness gradient may be used as the respective marker and, in the case of a fixed lag time, a fixed rotating pattern may be depicted by overlaying two such circles or markers. Any interruption or standstill of the image stream may thus be immediately identified with the assistance of the standstill in the rotation of the overlay pattern and any change in the lag time results in a change to the rotating pattern or rotating color distribution. One particularly advantageous configuration in this respect is further explained below.

If the respective marker is to be provided by displacement of the respective marker motif in dependency on the respective processing instant, a rectangular image segment may be used to represent the marker and displacement may proceed parallel to two sides of the rectangle. The displacement may proceed such that firstly the entire marker motif is displaced, after which that part of the marker motif that was pushed out of the image segment is reinserted into the image segment from the opposite side of the image segment. Thus, similarly to rotation, continuous periodic displacement is enabled. However, as a result, due to the explained state of flux, different portions of the marker motif are displaced in different directions.

The first and/or second markers and/or the first and/or second marker motifs may in each case be a linear, a circular, a circular ring-shaped, a circular segment-shaped, or a circular ring segment-shaped gradient of lightness and/or color saturation of a respective color or include this gradient. Alternatively, or additionally, hue may also change within the gradient. The gradient may be virtually continuous, such that the lightness and/or color saturation and/or hue may change in each pixel along the gradient path. It is, however, also possible for the gradient to be of coarser resolution, such that the lightness and/or color saturation and/or hue may change gradually in a number of, in particular in at least three, stages.

Apart from one portion of the marker or marker motif, the respective marker or marker motif may be formed in its entirety by the respective gradient, wherein the portion is of the same color over its entire area, in particular white or black, or is marked as transparent. In particular, the marker or marker motif in the portion cannot modify the image information overlaid with it, which may be achieved, for example, in the case of an additive overlay by setting all color channels to zero or by selecting the color as black.

The result of such a selection of markers or marker motifs is explained below on the basis of an example in which a green gradient is used in the first marker motif, the color saturation and/or lightness of which increases in the direction of displacement or rotation, and a red gradient is used as the second marker motif, the color saturation and/or lightness of which likewise increases in the direction of displacement or rotation. By selecting the location of the saturation or lightness maximum in the respective gradient, it is possible to provide that the location of the saturation or lightness maxima exactly coincides at the same angular position in the case of rotation or at the same position in the case of displacement when the lag time or difference in processing instants exactly corresponds to a tolerance time. In this case, the overlay results in a continuous yellow saturation or lightness gradient.

In the event of the lag time increasing from this tolerance time, an identical first processing instant would result in a later second processing instant and thus in greater displacement or rotation of the second marker motif. The color saturation or lightness maximum of the second marker thus projects beyond the color saturation or lightness maximum of the first marker and thus into a region in which the first marker has either a low color saturation or lightness or is even black or transparent, as has been explained above. This results in a substantially red stripe or a substantially red circle segment with strong saturation or lightness that alerts the user to the fact that the lag time has exceeded the tolerance time and the width of which is dependent on the extent to which the tolerance time has been exceeded.

Apart from this red stripe, the remaining overlay pattern forms a yellow color gradient and, in cases in which black or transparent portions of the respective marker are used, a purely green colored region also remains which does, however, have a low color saturation or lightness and thus does not stand out colorwise. When the lag time is too long, the image impression is thus dominated by the highly saturated red stripe or circle segment.

In contrast, if the lag time is below the tolerance time, the maximally saturated or light region of the first marker projects in the direction of displacement or rotation beyond the maximally saturated or light region of the second marker, so resulting in a green circle segment or a green stripe, the width of which again indicates how far below the tolerance time the lag time remains.

The explained example demonstrates that only little technical effort is required to achieve a highly intuitively graspable visualization of the lag time for a user. The same result may obviously be achieved if the direction of the color saturation or lightness gradient is reversed and at the same time the choice of green and red colors for the marker motifs is swapped. Although green and red are particularly clear signal colors for visualizing an unproblematic or problematic operating state, respectively, it may also be appropriate to use other colors for the respective gradients, for example, to enable adaptation to a user's color vision deficiencies.

In an alternative configuration, it may be possible to use a sequence of numbers or symbols as the first pattern or first pattern motif and a mask as the second pattern or second pattern motif, by which the first pattern or pattern motif is to be completely covered outside a particular segment or portion of the second pattern. In the case of an additive overlay, this may be achieved if the second pattern motif is black in a specific region in which the first pattern is to be identifiable and white in all other regions. In this case, the overlay pattern may display the lag time as a numerical value or the like.

In the method, an image stream of a plurality of temporally successive images, in particular an image stream from medical image data acquisition, may be transferred from the transmit facility to the receive facility, wherein, for each of the images, a visualization of the respective lag time is provided by overlaying the respective first and respective second markers. The visualization of the lag time is particularly appropriate for image data streams because changes in the lag time during image data streaming may be immediately identified by a change in the overlay pattern. Additionally, as has already been explained above, freezing of the image data stream, e.g., persistent display of the same image, may also be very rapidly identified.

Medical image data acquisition may be X-ray imaging, ultrasound imaging, or video imaging. Imaging may be provided by an imaging facility, for example, by an imaging facility arranged on a catheter or indeed by stationary acquisition facilities that image the patient or parts of the patient, for example, in order to track a catheter.

An operating input from a user may be acquired by the receive facility via an operating device, wherein the operating input or control information determined from the operating input is transferred from the receive facility to the transmit facility, after which the transmit facility actuates at least one actuator in dependency on the operating input or control information. The method may be used for remotely controlling any desired processes. For example, remote control may be provided for a robot or workpiece machining or for an actuator for a telemedicine application.

If the actuator serves to actuate an intervention device in a telemedicine context, the interaction between the intervention device and a patient may not be part of the method. For example, surgery carried out in a telemedicine context may proceed outside the claimed method.

In many use cases, the total lag including image acquisition and control may be less than 500 ms since longer total lags considerably impair hand-eye coordination. In some medical imaging processes, for example, in X-ray imaging, a lag of approx. 200 ms results merely from the imaging itself and it is assumed that roughly the same time is required for transfer of the operating input or control information as is required for transfer of the respective image, such that a tolerance time of, for example, approx. 150 ms may be maintained which the lag time may not be exceed.

The first and second marker motifs used may each be a circle in which one quadrant is black or transparent and the other three quadrants form the respective color saturation or lightness gradients. One complete rotation of the respective circle may here correspond to a change of the respective processing instant by 600 ms, such that the marker motifs may be selected. In the case of assumed identity of the first and second processing instants, the black or transparent quadrant of the second marker motif is offset by 90° contrary to rotation against the black or transparent quadrants of the first marker motif, such that in the event of a lag time which is equal to the tolerance time these black or transparent quadrants overlap and thus, as explained above, an overlay of the gradients without a colored stripe is obtained.

At least some of the final image data in the image segment may be evaluated by an evaluation algorithm in order to determine a measure of the lag time, wherein, when a trigger condition dependent on the measure is met, a warning signal is output to a user of the receive facility and/or a parameter of an imaging facility providing the image is adjusted and/or a parameter on which control of the actuator is dependent is adjusted. In the above example, in which a red and a green saturation or lightness gradient are used as the marker motifs, it may be checked whether a limit value for the red color channel is exceeded in the image segment for a pixel or for a minimum number of pixels and, at the same time, a limit value for the color value of the green color channel is not exceeded.

Although the method enables the user him/herself to directly estimate the actual lag time, it may nevertheless be appropriate by way of precaution additionally to indicate to the user that the lag time limit value is being exceeded or to adjust the settings of a device which is in use. For example, in the case of long lag times, maximum motion speeds and/or forces which may be provided by actuators controlled by operating inputs may be limited, and/or an attempt may be made to influence imaging, for example, in order to achieve higher frame rates and so compensate for unreasonably long lag times by reducing the time required for image acquisition. Alternatively, it may also be appropriate to reduce the imaging frame rate when the trigger condition is met, for example, to reduce radiation exposure during X-ray imaging. This may be appropriate since, in the case of long lags, actions may be carried out very slowly in medical procedures, for which reason lower frame rates may also be sufficient.

In addition to the method, the disclosure relates to a device for outputting at least one image with a transmit facility, a receive facility, and an output facility. The transmit facility is configured to: specify a first marker that is dependent on a first processing instant at which the image is processed by the transmit facility; process original image data of the image in such a manner that that part of the original image data that describes a specified image segment is modified by the first marker or an overlay of the first marker with the original image data in this image segment, in order to provide modified image data of the image; and transfer the modified image data to the receive facility. The receive facility is configured to: specify a second marker that is dependent on a second processing instant at which the image is processed by the receive facility; process the modified image data in such a manner that at least some of the modified image data in the specified image segment is modified by an overlay of the second marker with the modified image data in the image segment, in order to provide final image data of the image; and actuate the output facility in order to output the final image data, whereby a lag time which describes a time interval between the first and the second processing instants is visualized in the image segment of the image.

The device may serve to implement the computer-implemented method or the computer-implemented method may be executed during operation of the device. Irrespective thereof, the device may be further developed with the features mentioned in relation to the computer-implemented method and the advantages stated with regard to the features, and vice versa.

The receive facility may have an operating device configured to acquire a user's operating input, wherein the receive facility is configured to transfer the operating input or control information determined from the operating input from the receive facility to the transmit facility, wherein at least one actuator of the device is associated with the transmit facility, and wherein the transmit facility is configured to actuate the actuator in dependency on the operating input or the control information. Advantageous characteristics of such a facility for remotely controlling an actuator on the basis of a transferred image or image data stream have already been explained above in relation to the method.

The device may be a telemedicine device, wherein the actuator or at least a respective one of the actuators serves to actuate a component of a medical imaging facility of the device and/or an intervention device that interacts with a patient. Thus, not only may imaging processes be remotely controlled by using the device, but also telemedical surgical or interventional procedures or the like may be carried out.

The modified image data may be transmitted in the computer-implemented method or in the device via any desired communication links. A direct physical data line may be used as the communication link. The explained method or the explained device is, however, particularly advantageous if transfer times and/or processing times may vary, thus for example in the case of transfer in packet-switching networks or due to the use of data encryption. In one advantageous configuration, the modified image data may therefore be transferred via the internet or a virtual private network implemented via the latter. Any desired authentication and/or encryption methods, e.g., both methods which are already known and corresponding methods which are yet to be developed, may be used during transfer.

BRIEF DESCRIPTION OF THE DRAWINGS

Further advantages and details of the disclosure are revealed by the following exemplary embodiments and the associated drawings, in which, schematically.

DETAILED DESCRIPTION

Figure 1:
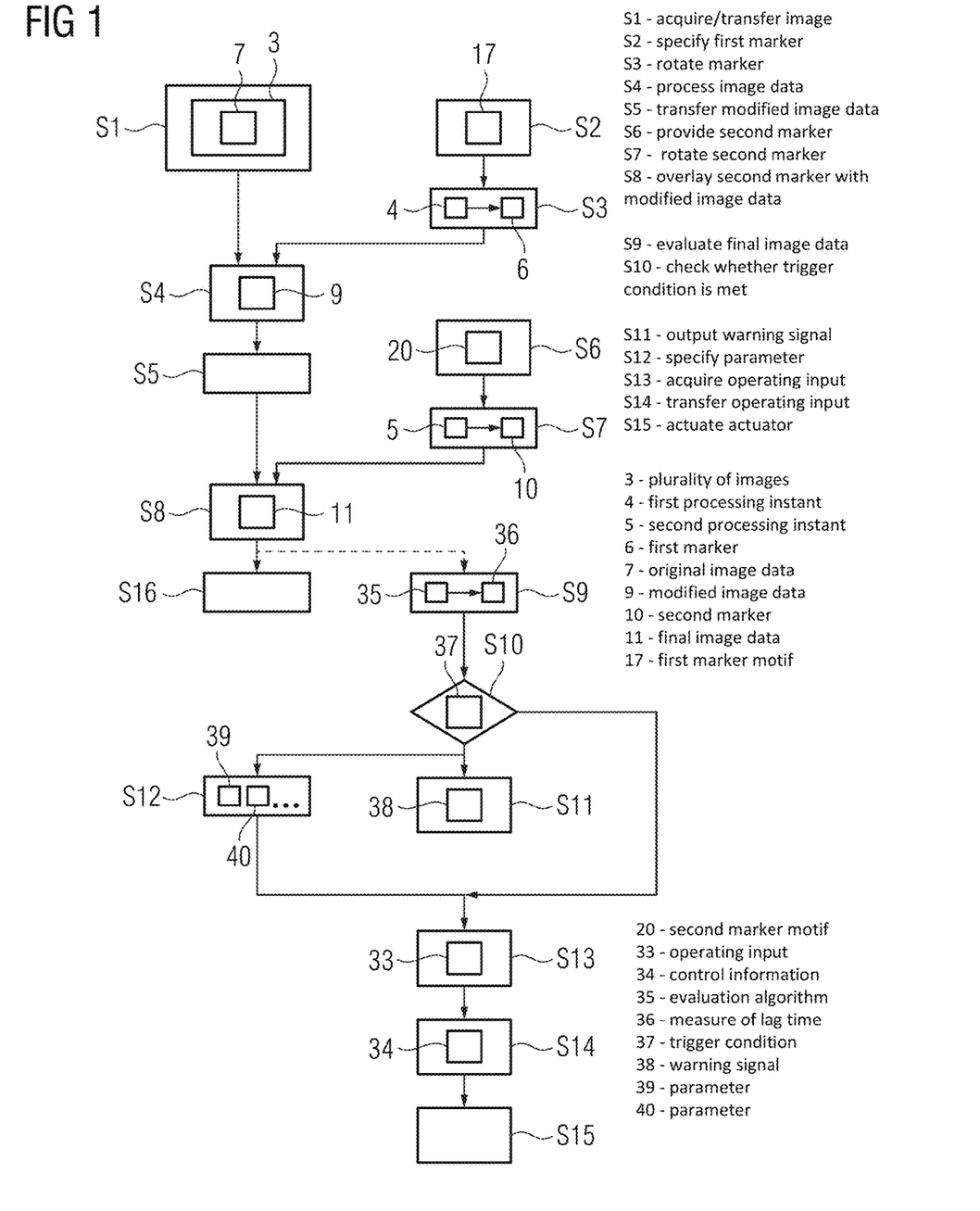
FIG. 1 depicts a flowchart of an example of a computer-implemented method for visualizing a lag time in at least one image transferred from a transmit facility to a receive facility.

FIG. 1 shows a flowchart of a computer-implemented method for visualizing a lag time in at least one image transferred from a transmit facility to a receive facility. The method is explained with additional reference to FIG. 2 which schematically shows an exemplary device by which the method may be implemented.

Figure 2:
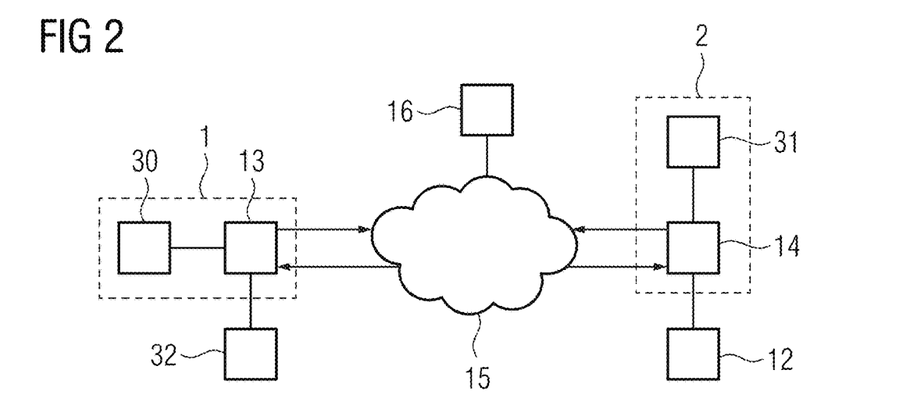
FIG. 2 depicts an embodiment of a device by which the method may be implemented.

For ease of understanding, a broad overview of the course of the method is provided before the method acts are addressed individually. A central concept here is that, at a first processing instant 4 at which the image 3 is processed by the transmit facility 1, (e.g., by a communication facility 13 of the transmit facility 1), a first marker 6 is specified that is dependent on the processing instant 4 at which this processing proceeds. This modifies (e.g., adds or replaces) the original image data 7 of the image 3 in an image segment 8 or is overlaid therewith, in order to provide modified image data 9, which is then transferred to the receive facility 2 or the communication facility 14 thereof. In the example, transfer proceeds via a packet-switching network 15, for example, the internet or a virtual private network implemented via the latter.

When the image 3 is processed by the receive facility 2, for example, by the communication facility 14 thereof directly after receipt, a second marker 10 is specified that is dependent on the second processing instant 5 at which processing by the receive facility 2 proceeds, and is overlaid with the modified image data 9 in the image segment 8 or in particular with the first marker 6 in order to provide final image data 11 which is output via the display facility 12.

Figure 3:
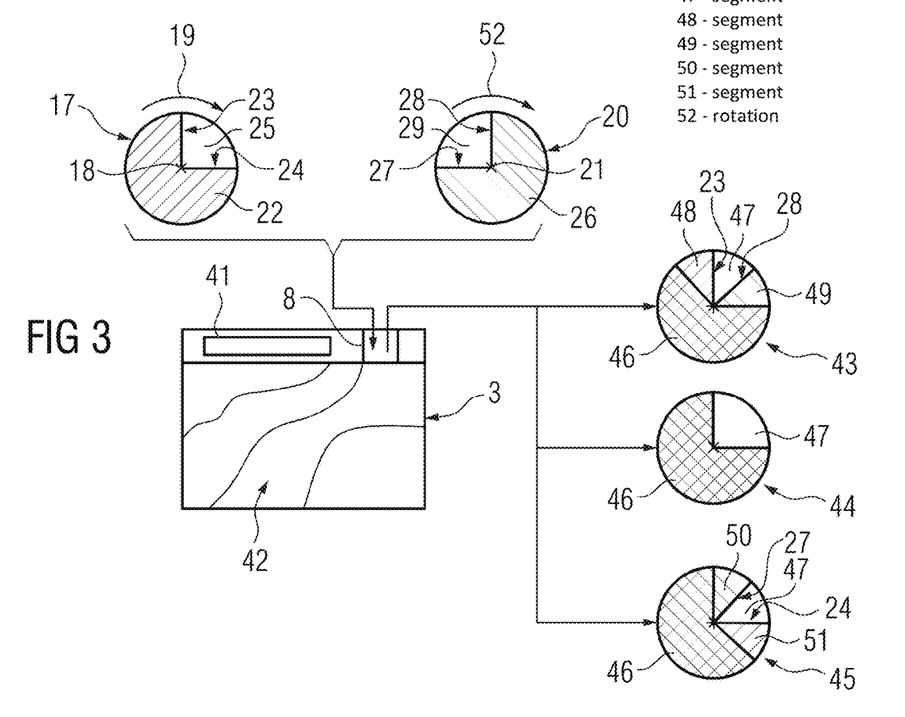
FIG. 3 depicts a schematic representation of possible marker motifs and their overlaying with the image data in the embodiment shown in FIG. 1.

As is explained in greater detail below on the basis of an example with reference to FIG. 3, overlaying the first and second markers 6, 10, which are specified in dependency on the respective processing instant 4, 5, allows the lag time, e.g., the interval between processing instants 4, 5, to be visualized for a user in a way that is easy to grasp intuitively.

In the example shown in FIG. 1, just one single image 3 is transferred and modified in order to visualize the lag time. However, as has already been explained herein, the described procedure is particularly advantageous if an image data stream or a sequence of images 3, which may be generated at a constant frame rate, is to be transferred and visualized.

In the configuration shown in FIG. 1, in act S1, the image 3 to be transferred or the original image data 7 thereof is first acquired by an imaging facility 30 of the transmit facility 1. If the device shown in FIG. 2 is, for example, a telemedicine device or if medical imaging images are to be transferred, the imaging facility 30 may be an ultrasonic sensor, an X-ray sensor, or a video camera.

The reference made in the explained method or explained device for outputting an image to medical imaging is, however, purely exemplary. The explained procedure or explained device may thus be used for image transfer, in particular in conjunction with remote control, e.g., also in the field of robotics or tool control.

Acts S2 and S3 serve to specify a first marker 6 in dependency on the first processing instant 4, at which the image 3 is processed by the transmit facility 1 or, in the example, specifically by the communication facility 13 thereof. In the example, as is explained in greater detail below with reference to FIG. 3, in act S2, a marker motif 17, which may be fixedly specified, is first specified and then, in act S3, is rotated about the axis of rotation 18 by an angle which is dependent on the first processing instant 4, as indicated by the arrow 19 in FIG. 3. Since rotations by a multiple of 360° result in the same marker 6, the first marker 6 varies periodically with the first processing instant 4. As has already been explained herein, a plurality of markers with differing periodicities may also be used. For simplicity's sake, however, the following explanation presumes the use of precisely one first and second marker.

In act S4, the original image data 7 of the image 3 is then processed by the transmit facility 1 in such a manner that that part of the original image data 7 that describes a specified image segment 8 is modified by the first marker 6. This is straightforwardly possible in the example shown in FIG. 3 since the segment 8 is arranged in a title line of the image 3 which may receive additional information 41, for example, patient data or capture parameters, whereby the image 42 of the patient tissue is not modified by the replacement of the original image data 7.

If no appropriate space is available in the image 3, the first marker 6 may alternatively be overlaid with the original image data 7 in segment 8. The information may nevertheless remain separable, for example, if the image 42 is black-and-white data while the marker 6 solely contains data in a color channel or the like.

As a result of inserting the first marker 6, modified image data 9 is available after act S4, which is transferred in act S5 to the receive facility 2 or the communication facility 14 thereof.

In acts S6 and S7, a second marker 10 is generated by the receive facility 2 or the communication facility 14 thereof which is dependent on the second processing instant 5, at which the image 3 is processed by the receive facility 2 or the communication facility 14. This proceeds similarly to the above-explained generation of the first marker 6. To this end, in act S6, a second marker motif 20 is first provided, as is shown by way of example in FIG. 3. In act S7, this is then rotated about an axis of rotation 21, as indicated by the arrow 52 in FIG. 3, wherein the angle of rotation is dependent on the second processing instant 5.

In act S8, the resultant second marker 10 is then overlaid with the modified image data 9 in the image segment 8 and thus with the first marker 6. An overlay pattern 43 to 45 is thus obtained which is dependent on the relative orientation of the first and second markers 6, 9 and thus on a time interval or a lag time between the first and second processing instants 4, 5. The resultant final image data 11 is output in act S16 by appropriate actuation of the display facility 12.

If a plurality of images 3 are transferred in succession, wherein the lag time between the respective first and second processing instants 4, 5 remains substantially unchanged, the same overlay pattern 43 to 45 is shown in all these images, wherein the latter is, however, rotated by a different angle of rotation due to the different processing instants of the images. A steady image stream is thus provided with a fixed rotating overlay representation such that freezing of the image stream may readily be identified. Changes in the lag time, for example, due to the transfer of image data via different routes, lead to a change in the overlay pattern itself. This is explained in greater detail below on the basis of the example shown in FIG. 3.

In this example, the first and second marker motifs 17, 20 are in each case circular and include a gradient 22, 26 of a color saturation and/or a lightness of a respective color. In the case of marker motif 17, the saturation and/or lightness of the color green varies within the gradient 22 from a maximum at the leading edge 23 in the direction of rotation to a minimum at the trailing edge 24 in the direction of rotation of the gradient 22. In the case of marker motif 20, the color saturation and/or lightness of the color red varies within the gradient 26 from a maximum at the leading edge 27 in the direction of rotation to a minimum at the trailing edge 28 in the direction of rotation. In the remaining portion 25, 29 of the respective marker motif 17, 20, all color channels are set to zero, such that these portions 25, 29 have no influence on the image data in the additive overlay of the resultant markers 6, 10 which is used.

The marker motifs 17, 20 thus differ on the one hand in terms of their angular position relative to one another and on the other hand with regard to the color of the respective gradient 22, 26. The different angular position may be selected such that it is compensated precisely when the lag time corresponds to a specified tolerance time.

If it is assumed by way of example that the first processing instant coincides with an angle of rotation of 0°, which would mean the first marker 6 is identical to the first marker motif 17, and that the lag time corresponds to an angle of rotation of 90° of the second marker motif 20 to provide the second marker 10, the colorless portions 25, 29 of the resultant markers 6, 10 will exactly coincide. This is shown by way of example for overlay representation 44 in FIG. 3. In this case, the circle segment 47 remains black since portions 25 and 29 have been overlaid there, and a yellow color gradient is obtained in circle segment 46 because the red and green color gradients of marker motifs 17, 20 are added together there.

In contrast, overlay representation 43 is obtained when the lag time corresponds merely to an angle of rotation of approx. 60°, e.g., when the lag time is below a tolerance time. In this case, circle segment 47 still remains black and circle segment 46 still displays a yellow saturation or lightness gradient. In contrast, the color in circle segment 48 is specified exclusively by the first marker motif 17, such that, due to the high color saturation and/or lightness in the region of the edge 23, a green region of high color saturation and/or lightness is obtained there.

In circle segment 49, in contrast, the color is exclusively specified by the second marker motif 20. A red region is thus obtained there, wherein the color saturation and/or lightness is, however, very low due to the low color saturation or lightness in the region of the edge 28, as a result of which circle segment 49 also appears at least approximately black.

A lag time below the tolerance time is thus visualized by displaying a distinctly identifiable green circle segment 48 next to the circle segment 46 with a yellow gradient, wherein the angular extent of circle segment 48 is dependent on how much the lag time is below the tolerance time.

In contrast, overlay representation 45 is obtained when the lag time exceeds the tolerance time. Circle segments 46, 47 are still respectively covered with a yellow saturation or lightness gradient or are black. The color in circle segment 50 is exclusively specified by the second marker motif 20, as a result of which a red color of high saturation or lightness is obtained. The color in circle segment 51 is exclusively specified by the first pattern motif 17, as a result of which a low green color saturation or lightness is obtained which continues to appear substantially black to an observer.

The tolerance time being exceeded by the lag time is thus marked by a clearly identifiable red color segment which follows the yellow color gradient, wherein the angular extent of red circle segment 50 is dependent on the extent to which the lag time exceeds the tolerance time.

On the basis of the overlay representations 43 to 45 shown in the image 3 or in image segment 8, a user may thus immediately identify how great a current lag time is or whether this time is above or below a specified tolerance time and how great the deviation from the tolerance time is.

Further advantageous configurations of markers 6, 10 or of marker motifs 17, 20, by which this outcome may likewise be achieved, have already been explained herein.

In some use cases, it may be advantageous additionally to evaluate the lag time automatically. One possible configuration for this purpose is illustrated by acts S9 to S11 in the example shown in FIG. 1.

In act S9, at least some of the final image data 11 in image segment 8 is evaluated by an evaluation algorithm 35 in order to determine a measure 36 of the lag time. For example, it may be evaluated whether there is a subsegment within image segment 8 in which there are high values in the red color channel and no or very low values in the other color channels. A measure 36 of the lag time may be the number of pixels in segment 8 for which this is the case.

In act S10, it is then checked whether a trigger condition 37 is met, which may in particular be the case if the lag time exceeds a tolerance time or exceeds it by a specified limit value or if the measure 36 exceeds a limit value.

If the trigger condition 37 is not met, no separate acts due to a long lag time are required, such that acts S13 to S15, which are explained below, may be carried out in the example.

In contrast, if the trigger condition 37 is met, a warning signal 38 may be output to a user of the receive facility 2 in act S11. For example, an acoustic, visual, or tactile warning may be provided to alert the user to the long lag time. This may be appropriate if the user is to remotely control a process on the basis of the transferred image or plurality of transferred images, as is explained below.

Additionally, or alternatively, a parameter 39 of the imaging facility 30 providing the image may be specified in act S12. This may be appropriate in order to increase a frame rate and thus reduce the additional lag required for imaging, which makes it possible to compensate for long transfer times or the like.

Additionally, or alternatively, it is also possible to adjust a parameter 40 on which control of the actuator 32 is dependent, which is explained below. When lag times are long, this may serve to reduce forces and/or displacement paths of actuators remotely controlled by the user in order to compensate for the greater sluggishness of operator response due to the lag time.

As has already been explained, the explained visualization of the lag time in the course of image transfer or processing may be particularly appropriate if a user to whom the respective image 3 is provided via the display device 12 is to remotely control processes on the basis of this image 3 or image sequence.

In order to enable such remote control, an operating input 33 may first be acquired via an operating device 31 of the receive facility 2 in act S13. The operating input 33 or the control information 34 determined therefrom are transferred back to the transmit facility 1 in act S14 and used there in act S15 to actuate the actuator 32.

Such control may be put to use in the field of robotics. Exemplary use cases are the remote control of a mobile robot, workpiece machining, or a telemedical application. Thanks to the visualization of the lag time, the user is aware of the extent to which the current image 3 relates to the current state of an imaged object, for example, a patient or medical instruments, or the extent to which the current image representation may no longer be current due to the long lag. This information may be taken into account in the course of remote control. Where lag times are relatively long, a user may accordingly act more cautiously and where lag times are very long, a user may refrain from critical acts or any operating input.

For example, if the device shown in FIG. 2 is intended to be a telemedicine device, the actuator 32 may control a component of a medical imaging facility, for example, an aperture or a C-arm, in order to adjust the imaging to the operator's preferences. Additionally, or alternatively, the or a further actuator 32 may actuate an intervention device by which a medical intervention may be performed under remote control or, for example, a catheter may be positioned.

Because the respective markers are specified by the transmit facility 1 or the receive facility 2, in each case, mutually independently in dependency on the respective processing instants 4, 5, the receive and transmit facilities 1, 2 are at least approximately time-synchronized. Although such synchronization may be performed directly between the transmit and receive facilities, it is appropriate to synchronize both the transmit facility 1 and the receive facility 2 via at least one common time server 16, in particular if the transmit facility 1 is to cooperate with a plurality of receive FACILITIES 2 and/or vice versa.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been illustrated and described in greater detail with reference to the embodiments, the disclosure is not restricted by the disclosed examples and other variations may be derived therefrom by a person skilled in the art without departing from the scope of protection of the disclosure. It is therefore intended that the foregoing description be regarded as illustrative rather than limiting, and that it be understood that all equivalents and/or combinations of embodiments are intended to be included in this description.

The invention claimed is:

1. A computer-implemented method for visualizing a lag time in an image transferred from a transmit facility to a receive facility, wherein the lag time describes a time interval between processing of the image by the transmit facility at a first processing instant and processing of the image by the receive facility at a second processing instant, the method comprising:
    specifying a first marker by the transmit facility, wherein the first marker is dependent on the first processing instant;
    processing original image data of the image by the transmit facility such that a part of the original image data that describes a specified image segment is modified by the first marker or an overlay of the first marker with the original image data in this image segment, therein providing modified image data of the image;
    transferring the modified image data from the transmit facility to the receive facility;
    specifying a second marker by the receive facility, wherein the second marker is dependent on the second processing instant;
    processing the modified image data by the receive facility such that at least part of the modified image data in the specified image segment is modified by an overlay of the second marker with the modified image data in the image segment, therein providing final image data of the image; and
    outputting the final image data by a display facility in order to visualize the lag time in the image segment of the image.

2. The computer-implemented method of claim 1, wherein the first marker is specified such that the first marker varies periodically with the first processing instant, and/or
    wherein the second marker is specified such that the second marker varies periodically with the second processing instant.

3. The computer-implemented method of claim 2, wherein the first marker is specified such that, in dependency on the first processing instant, a specified first marker motif is rotated with respect to the image segment and/or displaced at least in portions, and/or
    wherein the second marker is specified such that, in dependency on the second processing instant, a specified second marker motif is rotated with respect to the image segment and/or displaced at least in portions.

4. The computer-implemented method of claim 3, wherein one or more of the first marker, the second marker, the first marker motif, or the second marker motif comprises, in each case, a linear, a circular, a circular ring-shaped, a circular segment-shaped, or a circular ring segment-shaped gradient of lightness and/or color saturation of a respective color.

5. The computer-implemented method of claim 1, wherein the first marker is specified such that, in dependency on the first processing instant, a specified first marker motif is rotated with respect to the image segment and/or displaced at least in portions, and/or
    wherein the second marker is specified such that, in dependency on the second processing instant, a specified second marker motif is rotated with respect to the image segment and/or displaced at least in portions.

6. The computer-implemented method of claim 1, wherein an image stream of a plurality of temporally successive images is transferred from the transmit facility to the receive facility,
    wherein the image stream is from a medical image data acquisition, and
    wherein, for each image of the plurality of temporally successive images, a visualization of the respective lag time is provided by overlaying the respective first marker and the respective second marker.

7. The computer-implemented method of claim 1, further comprising:
    acquiring an operating input from a user by the receive facility via an operating device;
    transferring the operating input or control information determined from the operating input from the receive facility to the transmit facility; and
    actuating, by the transmit facility, at least one actuator in dependency on the operating input or the control information.

8. The computer-implemented method of claim 7, further comprising:
    evaluating at least some of the final image data in the image segment by an evaluation algorithm in order to determine a measure of the lag time; and
    outputting a warning signal to the user of the receive facility, adjusting a parameter of an imaging facility providing the image, adjusting a parameter on which control of the at least one actuator is dependent, or a combination thereof when a trigger condition dependent on the measure is met.

9. The computer-implemented method of claim 1, further comprising:
    evaluating at least some of the final image data in the image segment by an evaluation algorithm in order to determine a measure of the lag time; and
    outputting a warning signal to a user of the receive facility, adjusting a parameter of an imaging facility providing the image, adjusting a parameter on which control of an actuator is dependent, or a combination thereof when a trigger condition dependent on the measure is met.

10. A device for outputting an image, the device comprising:
- a transmit facility;
- a receive facility; and
- an output facility, wherein the transmit facility is configured to:
- specify a first marker that is dependent on a first processing instant at which the image is processed by the transmit facility;
- process original image data of the image in such a manner that a part of the original image data that describes a specified image segment is modified by the first marker or an overlay of the first marker with the original image data in the specified image segment, therein providing modified image data of the image; and
- transfer the modified image data to the receive facility, wherein the receive facility is configured to:
- specify a second marker that is dependent on a second processing instant at which the image is processed by the receive facility;
- process the modified image data in such a manner that at least some of the modified image data in the specified image segment is modified by an overlay of the second marker with the modified image data in the specified image segment, therein providing final image data of the image; and
- actuate the output facility to output the final image data, whereby a lag time that describes a time interval between the first processing instant and the second processing instant is visualized in the specified image segment of the image.

11. The device of claim 10, wherein the receive facility comprises an operating device configured to acquire an operating input of a user,
- wherein the receive facility is configured to transfer the operating input or control information determined from the operating input from the receive facility to the transmit facility,
- wherein at least one actuator of the device is associated with the transmit facility, and
- wherein the transmit facility is configured to actuate the actuator in dependency on the operating input or the control information.

12. The device of claim 11, wherein the device is a telemedicine device, and
- wherein the actuator or at least a respective actuator of the at least one actuator is configured to actuate a component of a medical imaging facility of the device and/or an intervention device that interacts with a patient.

* * * * *